United States Patent
Chong

(10) Patent No.: US 9,333,292 B2
(45) Date of Patent: May 10, 2016

(54) MECHANICALLY ACTUATED FLUID INFUSION DEVICE

(75) Inventor: Colin A. Chong, Burbank, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 989 days.

(21) Appl. No.: 13/533,797

(22) Filed: Jun. 26, 2012

(65) Prior Publication Data

US 2013/0345633 A1 Dec. 26, 2013

(51) Int. Cl.
*A61M 5/145* (2006.01)
*A61M 5/148* (2006.01)
*A61M 5/142* (2006.01)

(52) U.S. Cl.
CPC ............... *A61M 5/145* (2013.01); *A61M 5/148* (2013.01); *A61M 5/14244* (2013.01); *A61M 5/14248* (2013.01)

(58) Field of Classification Search
CPC ............ A61M 5/145; A61M 5/14244; A61M 5/14248; A61M 5/148
USPC ............... 604/131–134, 65–67; 128/DIG. 12, 128/DIG. 13
See application file for complete search history.

(56) References Cited

U.S. PATENT DOCUMENTS

| | | | |
|---|---|---|---|
| 3,151,616 A * | 10/1964 | Selfon | A61M 5/148 128/DIG. 12 |
| 3,631,847 A | 1/1972 | Hobbs, II | |
| 4,212,738 A | 7/1980 | Henne | |
| 4,265,241 A * | 5/1981 | Portner | A61M 5/14276 128/DIG. 12 |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |

(Continued)

FOREIGN PATENT DOCUMENTS

DE 4329229 3/1995
EP 0319268 11/1988

(Continued)

OTHER PUBLICATIONS

PCT Search Report (PCT/US02/03299), Oct. 31, 2002, Medtronic Minimed, Inc.

(Continued)

*Primary Examiner* — Manuel Mendez
(74) *Attorney, Agent, or Firm* — Ingrassia Fisher & Lorenz, P.C.

(57) ABSTRACT

A fluid infusion device, for delivery of a medication fluid to the body of a user, includes a housing, a fluid reservoir for the medication fluid, a dosing mechanism, an infusion component, and a mechanical actuator. The fluid reservoir and the dosing mechanism are located in the housing, and the dosing mechanism is coupled to receive the medication fluid from the fluid reservoir. The dosing mechanism has an adjustable fluid chamber that defines a variable dosage volume. The infusion component is coupled to the dosing mechanism to receive the medication fluid from the adjustable fluid chamber. The mechanical actuator is coupled to the dosing mechanism such that operation of the mechanical actuator causes the medication fluid to be expelled from the adjustable fluid chamber to the infusion component.

15 Claims, 11 Drawing Sheets

(56) References Cited

U.S. PATENT DOCUMENTS

| | | | |
|---|---|---|---|
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,098,409 A * | 3/1992 | Stock | A61M 5/1684 128/DIG. 12 |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,342,313 A * | 8/1994 | Campbell | A45F 3/20 222/103 |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,441,172 A * | 8/1995 | Yu | B65D 35/285 222/102 |
| 5,482,473 A | 1/1996 | Lord et al. | |
| 5,485,408 A | 1/1996 | Blomquist | |
| 5,497,772 A | 3/1996 | Schulman et al. | |
| 5,505,709 A | 4/1996 | Funderburk et al. | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,251,098 B1 * | 6/2001 | Rake | A61M 5/148 128/DIG. 12 |
| 6,259,937 B1 | 7/2001 | Schulman et al. | |
| 6,329,161 B1 | 12/2001 | Heller et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |

(56) References Cited

U.S. PATENT DOCUMENTS

| | | | |
|---|---|---|---|
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,828,764 B2 | 11/2010 | Moberg et al. | |
| 7,905,868 B2 | 3/2011 | Moberg et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0072733 A1* | 6/2002 | Flaherty | A61M 5/14248 604/890.1 |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2008/0269687 A1 | 10/2008 | Chong et al. | |
| 2009/0081951 A1 | 3/2009 | Erdmann et al. | |
| 2009/0082635 A1 | 3/2009 | Baldus et al. | |
| 2009/0299290 A1 | 12/2009 | Moberg | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO2009/102355 A2 | 8/2009 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(Intensive Diabetes Management, 1995). Insulin Infusion Pump Therapy. pp. 66-78.

Disetronic My Choice™ D-TRON™ Insulin Pump Reference Manual. (no date).

Disetronic H-TRON® plus Quick Start Manual. (no date).

(56) References Cited

OTHER PUBLICATIONS

Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, vol. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, vol. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifii-

(56) References Cited

OTHER PUBLICATIONS cal Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

MECHANICALLY ACTUATED FLUID INFUSION DEVICE

TECHNICAL FIELD

Embodiments of the subject matter described herein relate generally to medical devices such as fluid infusion devices. More particularly, embodiments of the subject matter relate to a low cost, mechanically actuated insulin infusion pump.

BACKGROUND

Certain diseases or conditions may be treated, according to modern medical techniques, by delivering a medication or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., insulin pumps) to deliver controlled amounts of insulin to a patient.

A fluid infusion device suitable for use as an insulin pump may be realized as an external device or an implantable device that is surgically implanted into the body of the patient. External fluid infusion devices include devices designed for use in a generally stationary location (for example, in a hospital or clinic), and devices configured for ambulatory or portable use (to be carried by a patient). External fluid infusion devices may establish a fluid flow path from a fluid reservoir to the patient via, for example, a suitable hollow tubing. The hollow tubing may be connected to a hollow fluid delivery needle that is designed to pierce the patient's skin to deliver an infusion medium to the body. Alternatively, the hollow tubing may be connected directly to the patient's body through a cannula or set of micro-needles.

Portable insulin pump devices can be expensive to procure and maintain due to their extensive use of sensitive electronic components, batteries, microprocessor chips, electronic display elements, motors, controllers, and the like. Consequently, many diabetes patients continue to use the traditional low cost approach that involves patient-actuated syringes. Accordingly, it would be desirable to have a low cost portable fluid infusion pump device that need not rely on expensive electronic components for fluid delivery operations. Furthermore, other desirable features and characteristics will become apparent from the subsequent detailed description and the appended claims, taken in conjunction with the accompanying drawings and the foregoing technical field and background.

BRIEF SUMMARY OF EMBODIMENTS

An embodiment of a fluid infusion device is disclosed. The fluid infusion device is designed to deliver a medication fluid to the body of a user. The fluid infusion device includes a housing, a fluid reservoir for the medication fluid, a dosing mechanism, an infusion component, and a mechanical actuator. The fluid reservoir and the dosing mechanism are both located in the housing. The dosing mechanism is coupled to the fluid reservoir to receive the medication fluid from the fluid reservoir. The dosing mechanism includes an adjustable fluid chamber that defines a variable dosage volume. The infusion component is coupled to the dosing mechanism to receive the medication fluid from the adjustable fluid chamber. The mechanical actuator is also coupled to the dosing mechanism. Operation of the mechanical actuator causes the medication fluid to be expelled from the adjustable fluid chamber to the infusion component.

Another embodiment of a fluid infusion device is also disclosed. The fluid infusion device includes a housing, a fluid reservoir for the medication fluid, a valve assembly located in the housing, a dosing mechanism located in the housing, and a fluid conduit. The medication fluid in the fluid reservoir is maintained under positive pressure. The valve assembly is coupled to the fluid reservoir, and the dosing mechanism is coupled to the fluid reservoir via the valve assembly. The dosing mechanism includes an adjustable fluid chamber that defines a user-selectable dosage volume. The dosing mechanism also includes a mechanical actuator. The fluid conduit is coupled to the dosing mechanism via the valve assembly. At least a portion of the fluid conduit is external to the housing when the fluid infusion device is deployed for operation. Application of an actuation force to the mechanical actuator initiates a fluid delivery operation, and removal of the actuation force from the mechanical actuator initiates a refill operation. During the fluid delivery operation, the valve assembly allows the medication fluid to flow from the adjustable fluid chamber into the fluid conduit for delivery to the body of the patient, while inhibiting flow of the medication fluid from the adjustable fluid chamber into the fluid reservoir. During the refill operation, the valve assembly allows the medication fluid to flow from the fluid reservoir into the adjustable fluid chamber, while inhibiting flow of the medication fluid from the fluid reservoir into the fluid conduit.

Also provided here is an embodiment of a fluid infusion device for delivery of a medication fluid to the body of a user. The fluid infusion device includes a housing, a fluid reservoir to maintain the medication fluid under positive pressure, wherein the fluid reservoir is located in the housing, and a valve assembly located in the housing and coupled to the fluid reservoir. The fluid infusion device also includes a dosing mechanism located in the housing and coupled to the fluid reservoir via the valve assembly. The dosing mechanism includes a mechanical actuator to adjust a fluid chamber of the dosing mechanism such that the fluid chamber defines a user-selectable dosage volume. The fluid infusion device also includes a fluid delivery conduit coupled to the dosing mechanism via the valve assembly. In response to application of force to the mechanical actuator, the medication fluid in the fluid chamber is expelled through the fluid delivery conduit, while the valve assembly inhibits flow of the medication fluid from the fluid chamber to the fluid reservoir. In response to removal of the force, the mechanical actuator automatically retracts to refill the fluid chamber with the medication fluid from the fluid reservoir, while the valve assembly inhibits flow of the medication fluid from the fluid reservoir to the fluid delivery conduit and inhibits fluid flow from the fluid delivery conduit to the fluid chamber.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
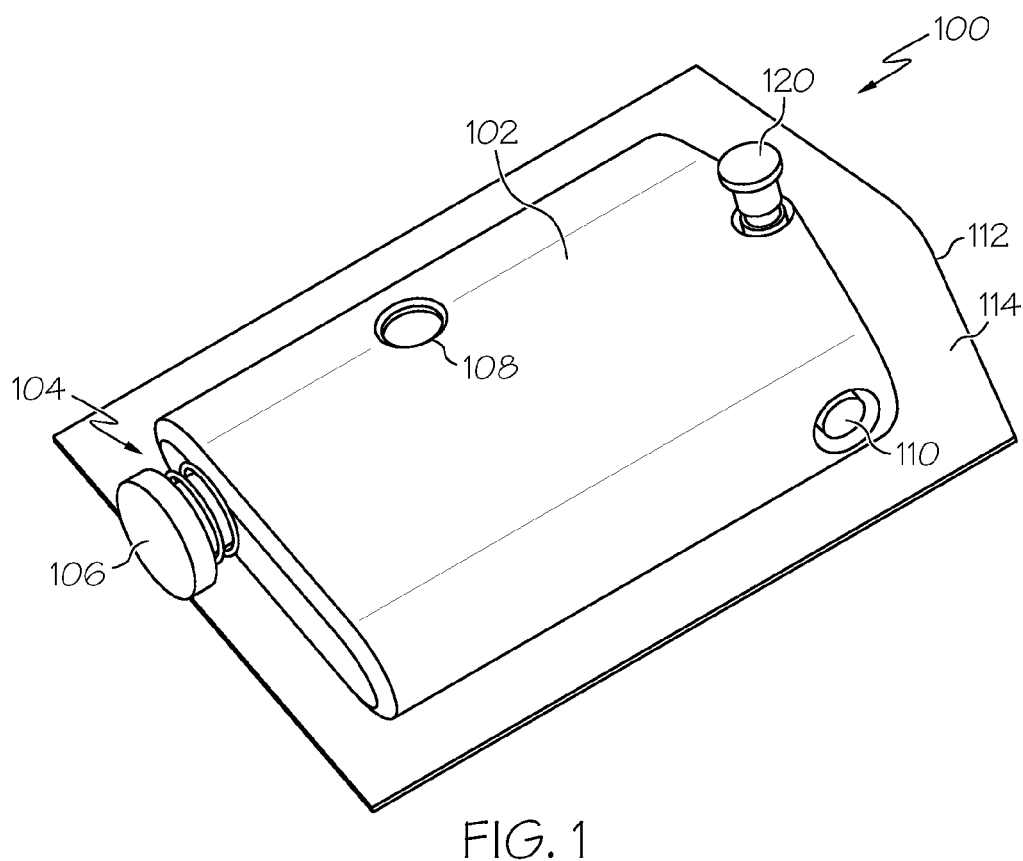
FIG. 1 is a perspective view of an exemplary embodiment of a mechanically actuated fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" may be used to refer to directions in the drawings to which reference is made. Terms such as "front", "back", "rear", "side", "outboard," and "inboard" may be used to describe the orientation and/or location of portions of a component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The following description relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and subcutaneous fluid delivery components may not be described in detail here. Examples of infusion pumps and/or related pump drive systems used to administer insulin and other medications may be of the type described in, but not limited to: United States patent application number 2009/0299290 A1; United States patent application number 2008/0269687; U.S. Pat. No. 7,828,764; and U.S. Pat. No. 7,905,868 (the entire content of these patent documents is incorporated by reference herein).

The subject matter described here relates to various features, components, operating methodologies, and technology associated with a mechanical fluid infusion device. The fluid infusion device is "mechanical" in that it need not (and preferably does not) rely on any electronic components or power supply to support its primary fluid delivery operations. In certain exemplary embodiments, the activation and/or actuation of the fluid delivery function is achieved in a fully mechanical manner. Accordingly, an embodiment can be deployed with minimal or no electronic or electrical elements, components, power sources, sensors, motors, or the like. For this reason, a practical implementation of the mechanical fluid infusion device can be manufactured in a very cost efficient manner to provide a low cost alternative to the modern electronic and processor based infusion devices that are currently available. Moreover, the mechanical fluid infusion device could be designed to be a disposable single-use item, due to its low manufacturing cost.

Figure 2:
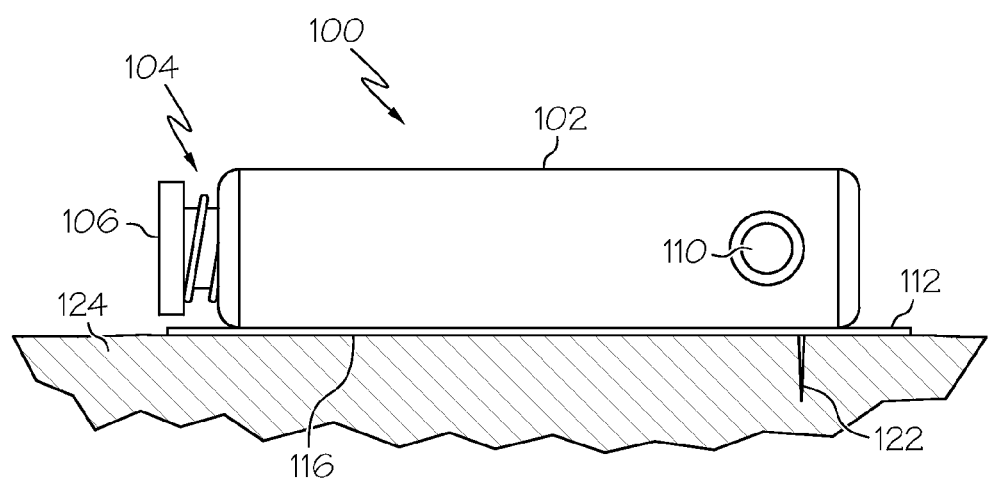
FIG. 2 is a side view of the fluid infusion device shown in FIG. 1 after attachment to the body of a user.

Turning now to the drawings, FIG. 1 is a perspective view of one exemplary embodiment of a mechanically actuated fluid infusion device 100 prior to deployment, and FIG. 2 is a side view of the fluid infusion device 100 after attachment to the body of a user. The fluid infusion device 100 includes an outer housing 102 that represents the primary structural component of the fluid infusion device 100. The housing 102 may be fabricated from a lightweight and tough material such as a molded plastic material. In practice, the housing 102 may be fabricated in two or more pieces that are assembled to form a shell for various internal components of the fluid infusion device 100. For example, the housing 102 may be manufactured in two halves that are bonded, welded, or otherwise attached together to enclose the internal components.

The fluid infusion device 100 includes a mechanical actuator 104 (e.g., a plunger, a dispensing unit, or the like) that is operated to deliver a metered dose of fluid to the body of the patient. As depicted in FIG. 1, the mechanical actuator 104 may terminate at a knob 106 that protrudes from the outer housing 102. For this particular embodiment, the user actuates (e.g., presses down on) the knob 106 to activate the fluid delivery operation of the fluid infusion device 100. The housing 102 may incorporate or cooperate with one or more safety features to reduce the likelihood of accidental fluid delivery. For example, the housing 102 may include a locking mechanism for the knob 106 (e.g., a switch, a button, a slider, or the like) that must be released to actuate the knob 106. As another example, the housing 102 may include one or more structural features that make it difficult for the knob 106 to be inadvertently actuated (e.g., a hood feature, guard tabs surrounding the knob 106, or the like).

Moreover, rotation of the knob 106 adjusts the volume of a fluid chamber (hidden from view in FIG. 1) such that a metered amount of fluid can be administered with each activation of the mechanical actuator. This adjustment feature is described in more detail below with reference to FIGS. 4 and 13-16. In this regard, the fluid infusion device 100 may include a feature that indicates the dosage volume setting to the user. For example, the housing 102 may include a slot, a window, or an opening 108 formed therein. After adjusting the dosage volume to the desired setting, an identifier of the current volume setting will appear within the opening 108. In practice, labels, numbers, color codes, symbols, or any type of indicia can be used for this purpose. For example, the fluid infusion device 100 may be suitably configured to provide a plurality of predetermined and calibrated dosage volumes, such that the desired dosage setting is visible within the opening 108 (e.g., 1 Unit, 5 Units, 10 Units, or any quantity or measurement using any convenient or standardized unit of measure).

The fluid infusion device 100 may also include a fill port 110 that is accessible from outside the housing 102. The fill port 110 is fluidly coupled to a fluid reservoir (not visible in FIG. 1) that is located inside the housing 102. The fill port 110 is suitably configured to facilitate filling of the fluid reservoir with the desired fluid, e.g., a medication fluid such as insulin. Depending upon the embodiment and/or the desired application, the fill port 110 could be designed to accommodate filling of the fluid reservoir at the time of manufacture or to accommodate filling (and, in certain implementations, refilling) by the end user, a caregiver, a physician, or the like. In accordance with one embodiment, the fill port 110 includes a small opening or hole that accommodates a syringe needle such that a syringe can be used to fill the internal fluid reservoir. Moreover, the fill port 110 is preferably designed to be self-sealing such that the medication fluid does not leak out of the fill port 110 after the internal fluid reservoir has been filled. To this end, the fill port 110 may employ a resilient sealing element (such as a septum) through which the filling needle passes during the filling operation. In an alternative embodiment designed to be a single use and disposable unit, the internal fluid reservoir may be provided in a pre-filled state (filled during manufacturing), rendering the fill port 110 unnecessary.

The illustrated embodiment of the fluid infusion device 100 is intended to be affixed to the skin of the patient. Accordingly, the fluid infusion device 100 may include an adhesive patch 112 or an adhesive layer having a first side 114 affixed to the housing 102 and having a second side 116 (see FIG. 2) for attachment to the body of the patient. The second side 116 of the adhesive patch 112 may be provided to the user with a removable liner (not shown) that is removed and discarded prior to use. Thus, the adhesive patch 112 allows the patient or caregiver to secure the fluid infusion device 100 to a convenient and discreet location on the body of the patient, as desired.

This particular embodiment of the fluid infusion device 100 includes an introducer 120 (see FIG. 1) that is used to insert a fluid delivery conduit 122 (see FIG. 2) into the skin of the patient. The fluid delivery conduit 122 is one suitable embodiment of an infusion component that is integrated with the housing 102 to accommodate direct attachment of the fluid infusion device 100 to the body of the user. The introducer 120 may include a needle that facilitates subcutaneous insertion of a flexible fluid delivery conduit 122, e.g., a tube or a cannula. Thus, after the housing 102 is affixed to the skin 124 of the patient, the introducer 120 can be manipulated to insert the fluid delivery conduit 122 into the body of the patient. Accordingly, when the fluid infusion device 100 is deployed for operation in this manner, at least a portion of the fluid delivery conduit 122 is external to the housing 102. The introducer 120 can be removed and discarded after insertion of the fluid delivery conduit 122. Accordingly, the introducer 120 does not appear in FIG. 2. After deployment, the fluid delivery conduit 122 functions as one part of the fluid delivery path associated with the fluid infusion device 100, as is well understood.

Figure 3:
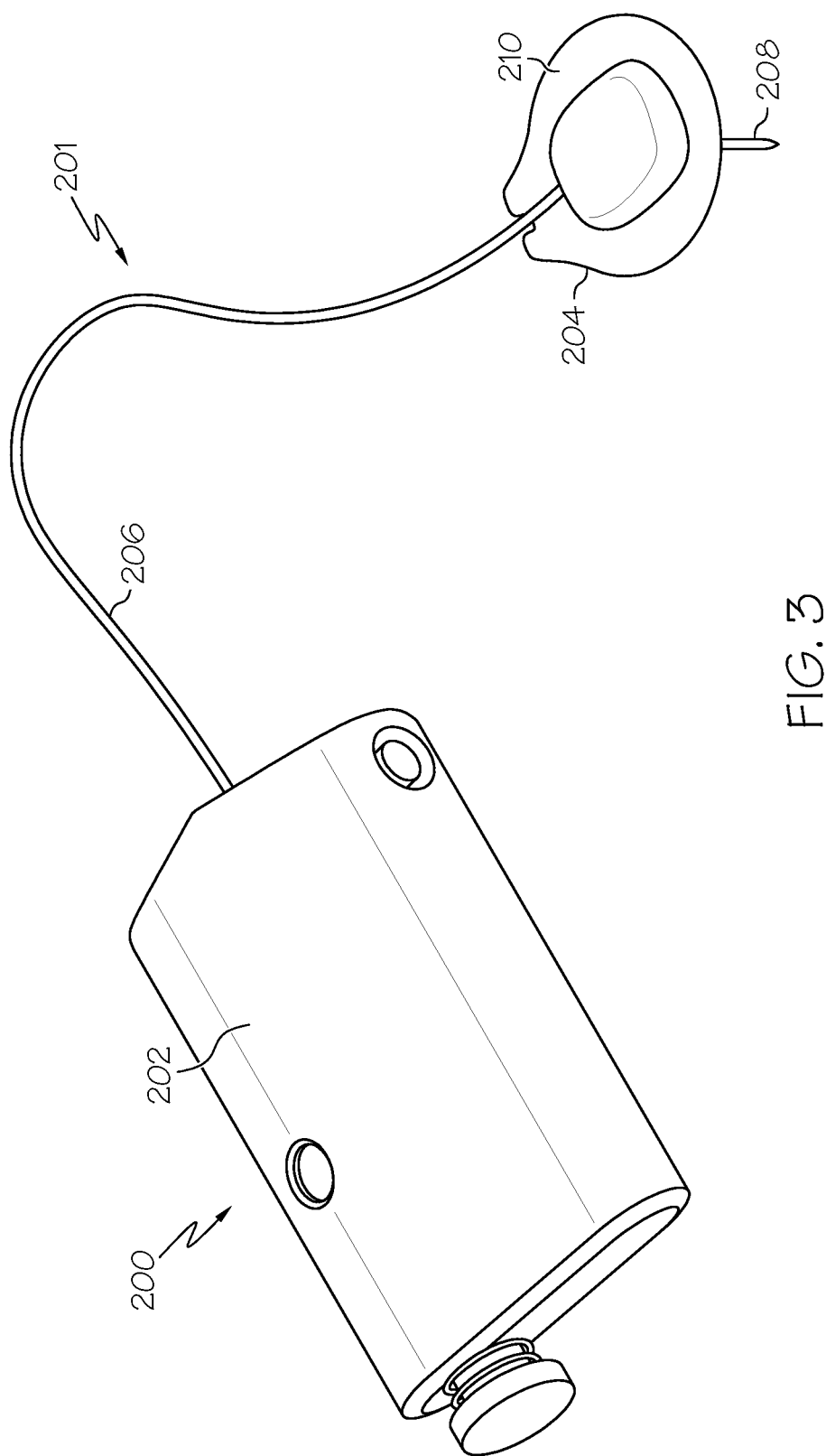
FIG. 3 is a perspective view of another exemplary embodiment of a mechanically actuated fluid infusion device, shown with an infusion set component.

FIG. 3 is a perspective view of another exemplary embodiment of a mechanically actuated fluid infusion device 200. The fluid infusion device 200 is similar in many respects to the fluid infusion device 100 described above. The fluid infusion device 200, however, cooperates with an infusion component 201 that is remote from the housing 202 of the fluid infusion device 200. More specifically, the illustrated embodiment of the infusion component 201 includes an infusion set 204 and tubing 206 coupled between the infusion set 204 and the fluid source (not shown) located within the housing 202. The infusion set includes a cannula 208 for subcutaneous insertion into the body of the user. Accordingly, the tubing 206 establishes and maintains a fluid flow path from the fluid source to the infusion set 204 and to the cannula 208. The infusion set 204 may include an adhesive element 210 to accommodate direct attachment of the infusion set 204 to the body of the user. In practice, the fluid infusion device 200 could be affixed to the body of the patient (as described above for the fluid infusion device 100), or it could be carried or worn by the patient in an appropriate manner (e.g., using a belt clip, in a pocket, or strapped to the body).

Figure 4:
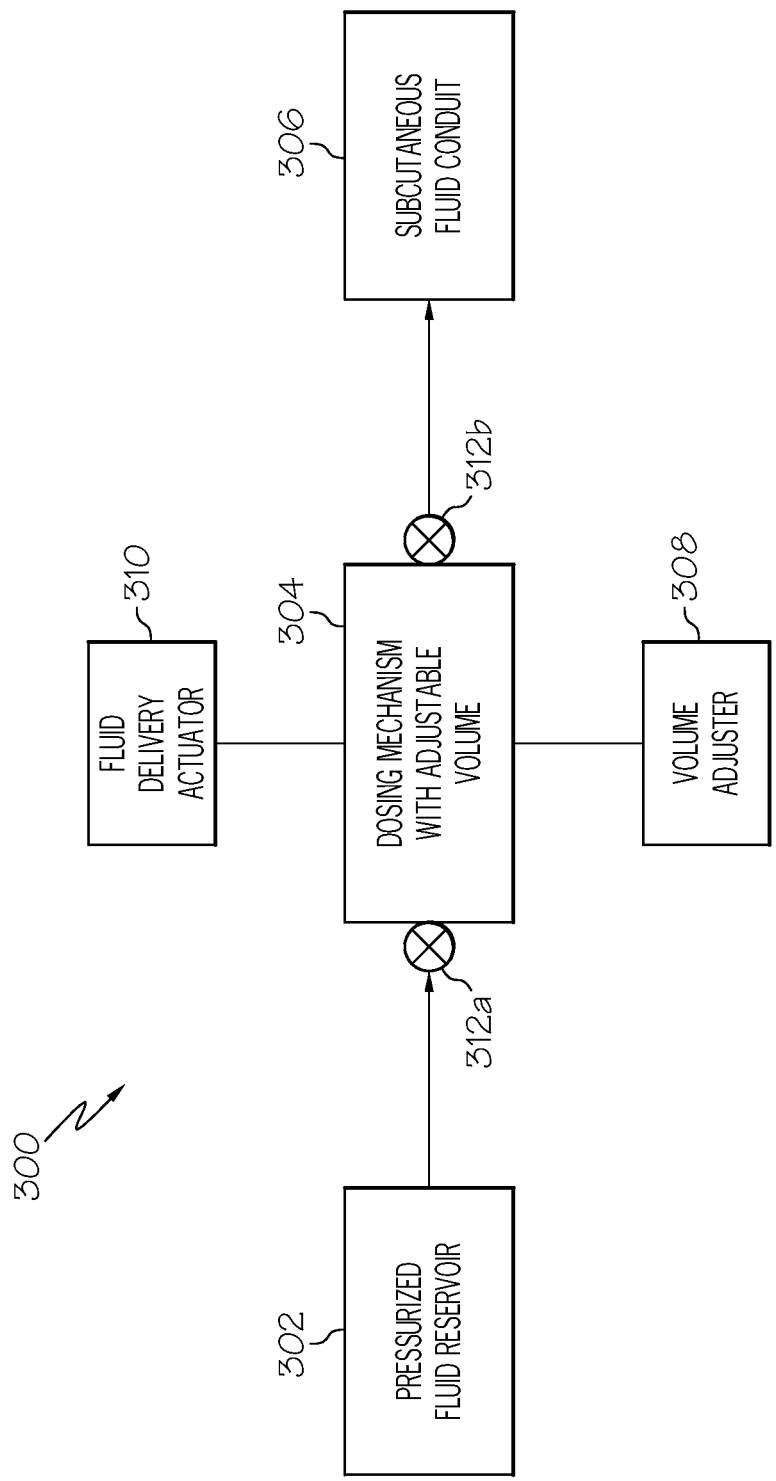
FIG. 4 is a schematic representation of various components of a mechanical fluid infusion device.

FIG. 4 is a schematic representation of various components of an exemplary embodiment of a mechanical fluid infusion device 300 that is suitably configured to deliver a medication fluid to the body of a user in response to user actuation. The components depicted in FIG. 4 may be found in an embodiment of the fluid infusion device 100 (FIG. 1) and in an embodiment of the fluid infusion device 200 (FIG. 3). The illustrated embodiment of the fluid infusion device 300 generally includes, without limitation: a pressurized fluid reservoir 302; a dosing mechanism 304 having an adjustable fluid chamber that defines a variable dosage volume; a subcutaneous fluid conduit 306; a volume or dosage adjuster 308; and a mechanical fluid delivery actuator 310. The fluid infusion device 300 may also incorporate a suitably configured valve assembly 312 having one or more fluid valves to regulate the flow of the medication fluid throughout the fluid infusion device 300 and to regulate the delivery of the medication fluid from the fluid infusion device 300. It should be appreciated that FIG. 4 represents a simplified functional representation of the fluid infusion device 300, and that a working implementation of the fluid infusion device 300 may (and usually will) include additional elements, components, and structure that is neither shown nor described in detail here. FIG. 4 is presented here to provide a foundation for the following description of the general functionality of the mechanically actuated fluid infusion device 300.

The fluid reservoir 302 may be provided as a pre-filled component, or it may be designed to accommodate filling by the end user, a caregiver, or the like. The fluid reservoir 302 holds a quantity of medication fluid and serves as the source of the medication fluid for the fluid infusion device 300. For the exemplary embodiments described here, the fluid reservoir 302 is located and held in place in the housing (not shown in FIG. 4) of the fluid infusion device 300. The fluid reservoir 302 is pressurized in that the medication fluid in the fluid reservoir 302 is maintained under positive pressure using an appropriate methodology, technique, or structure. In other words, the medication fluid is held under pressure that would normally force the medication fluid out of the fluid reservoir 302. The valve assembly 312 may include an inlet valve 312a between the fluid reservoir 302 and the dosing mechanism 304, wherein the inlet valve 312a regulates flow of the medication fluid from the fluid reservoir 302 to the dosing mechanism 304. For example, the inlet valve 312a may be realized as a one-way valve that inhibits flow of the medication fluid from the adjustable fluid chamber of the dosing mechanism 304 to the fluid reservoir 302.

The dosing mechanism 304 is also located inside the housing of the fluid infusion device 300, and is coupled to the fluid reservoir 302 to receive the medication fluid from the fluid reservoir 302 as needed. The dosing mechanism 304 has an adjustable fluid chamber that can be configured and set—by the patient, a caregiver, the manufacturer, the vendor, a physician, or the like—by manipulating the volume adjuster 308. The volume adjuster 308 may be realized as one or more knobs, switches, buttons, sliders, levers, etc. In certain embodiments, the dosing mechanism 304 accommodates a plurality of different user-selectable and/or calibrated fluid delivery volumes (such as 1 Unit, 5 Units, and 10 Units), wherein only the pre-set volumes can be selected. Thus, the adjustable fluid chamber may be adjustable in discrete steps that define a plurality of predetermined and calibrated dosage volumes for the dosing mechanism 304. In an alternative embodiment, the dosing mechanism 304 is continuously variable (between a minimum volume and a maximum volume) to provide the user with greater flexibility and more options. Once adjusted and set, however, the dosing mechanism 304 defines an accurate and metered dose of the medication fluid.

Each fluid delivery operation results in the delivery of one metered dose, as determined by the adjustable volume of the dosing mechanism 304. Thus, if the fluid delivery volume is set at one Unit and the patient desires to administer a bolus of five Units, then the fluid delivery actuator 310 must be manipulated five times in succession to deliver a total of five Units. As another example, if the volume is set at five Units, then the fluid delivery actuator 310 must be activated twice to deliver a bolus of ten Units. Depending upon the particular implementation, the fluid delivery actuator 310 may be realized as a switch, a button, a lever, a plunger, or any suitably configured mechanical component. In an exemplary embodiment, the fluid delivery actuator 310 is realized as a mechanical plunger for the adjustable fluid chamber of the dosing mechanism 304.

Operation of the fluid delivery actuator 310 forces the medication fluid out of the fluid chamber of the dosing mechanism 304, and causes the medication fluid to be expelled from the fluid chamber to the fluid conduit 306, which represents one suitable embodiment of an infusion component for the fluid infusion device 300. In this regard, the fluid conduit 306 is coupled to the dosing mechanism 304 to receive the medication fluid from the adjustable fluid chamber as needed. As mentioned above with reference to FIGS. 1-3, the fluid conduit 306 may be a rigid needle or a soft cannula that extends directly from the housing of the fluid infusion device 300, or it may be a rigid needle or a soft cannula associated with an infusion set component that is fluidly coupled to the fluid infusion device 300 using a tube.

The valve assembly 312 may include an outlet valve 312b between the dosing mechanism 304 and the fluid conduit 306, wherein the outlet valve 312b regulates flow of the medication fluid from the adjustable fluid chamber of the dosing mechanism 304 to the fluid conduit 306. In this regard, the outlet valve 312b may be realized as a one-way valve that inhibits flow of the medication fluid from the fluid conduit 306 to the dosing mechanism 304. Moreover, the valve assembly 312 may be suitably configured to inhibit flow of the medication fluid from the fluid reservoir 302 directly to the fluid conduit 306. In other words, the valve assembly 312 may be designed to ensure that fluid from the fluid reservoir 302 must flow into the adjustable fluid chamber of the dosing mechanism 304 before it flows to the fluid conduit 306.

FIG. 4 schematically depicts the dosing mechanism 304, the volume adjuster 308, and the fluid delivery actuator 310 as distinct functional elements. In practice, however, the dosing mechanism and the mechanical fluid delivery actuator 310 could form an integrated subassembly of the fluid infusion device 300. Similarly, the dosing mechanism and the volume adjuster 308 could be fabricated as an integrated subassembly. In yet another embodiment, the dosing mechanism 304, the volume adjuster 308, and the fluid delivery actuator 310 are realized as a single cooperating subassembly (as described below with reference to FIGS. 9-16).

As mentioned above, the medication fluid may be held under positive pressure to facilitate the fluid delivery action of the fluid infusion device. Accordingly, the fluid reservoir may be referred to here as a pressurized fluid reservoir. In this regard, a pressurized fluid reservoir can be achieved using a variety of reservoir configurations, as desired for the particular application. For example, FIGS. 5-8 schematically depict four different ways in which medication fluid can be maintained under positive pressure in the context of a fluid infusion device of the type described here. These examples are not intended to be exhaustive or to limit the scope and application of the embodiments presented here. Indeed, a pressurized fluid reservoir could be implemented using other techniques, components, and structures not shown or described in detail here.

Figure 5:
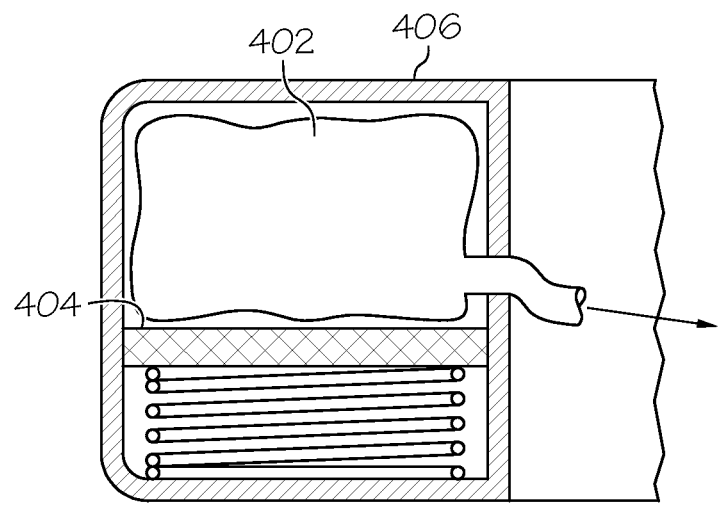
FIG. 5 is a simplified schematic side view of an embodiment of a pressurized fluid reservoir that cooperates with a force-imparting structure.

FIG. 5 is a simplified schematic side view of an embodiment of a pressurized fluid reservoir 402 that cooperates with a force-imparting structure 404. For this embodiment, the fluid reservoir 402 is realized as a resilient and compressible bladder or bag. Therefore, the fluid reservoir 402 could be fabricated from any flexible material that does not react with the medication fluid. The fluid reservoir 402 may be positioned within an interior pocket or cavity formed within the housing 406 of the fluid infusion device. The structure 404 is operatively coupled to the fluid reservoir 402 to impart a compressive force to the fluid reservoir 402. In this regard, the structure 404 may include or cooperate with a spring 408 or any suitable biasing element to form a spring loaded platform for the fluid reservoir 402. In accordance with this arrangement, the structure 404 (e.g., the spring loaded platform) squeezes the resilient bladder of the fluid reservoir 402 against an interior surface of the housing 406 such that the external force on the bladder places the medication fluid in the bladder under positive pressure. Accordingly, the medication fluid naturally flows out of the fluid reservoir 402 (in the direction indicated by the arrow) unless the flow is inhibited by the valve assembly of the fluid infusion device. It should be appreciated that more than one force imparting structure could be deployed to compress the fluid reservoir 402 within the housing 406. Moreover, the direction(s) in which the fluid reservoir 402 is compressed may vary from one embodiment to another.

Figure 6:
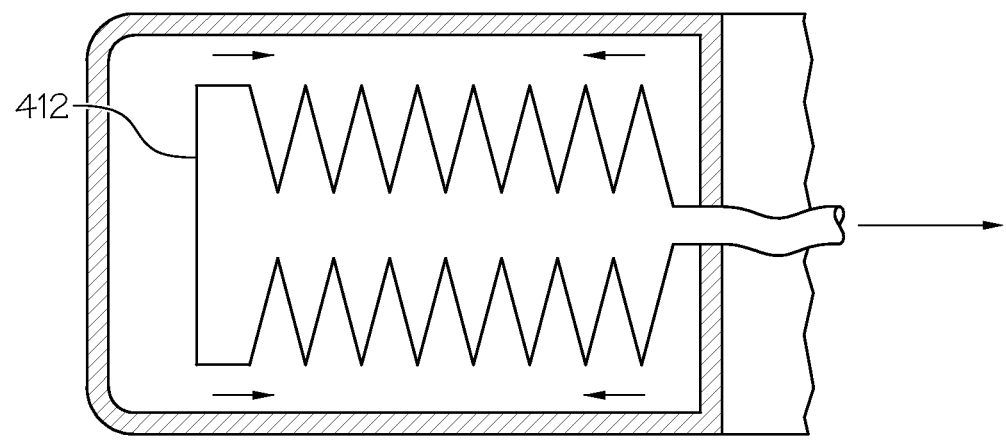
FIG. 6 is a simplified schematic side view of an embodiment of a self-contracting fluid reservoir.

FIG. 6 is a simplified schematic side view of an embodiment of a self-contracting fluid reservoir bag 412 that is suitable for use as a fluid reservoir for medication fluid. The reservoir bag 412 is realized as a self-contracting resilient bellows that naturally tends to "shrink" upon itself, as indicated by the opposing horizontal arrows in FIG. 6. Thus, the reservoir bag 412 expands in volume when filled with the medication fluid, and such expansion inherently places the medication fluid under positive pressure. Accordingly, the medication fluid naturally flows out of the reservoir bag 412 (in the direction indicated by the outgoing arrow) unless the flow is inhibited by the valve assembly of the fluid infusion device. Moreover, the reservoir bag 412 naturally shrinks as the medication fluid exits.

Figure 7:
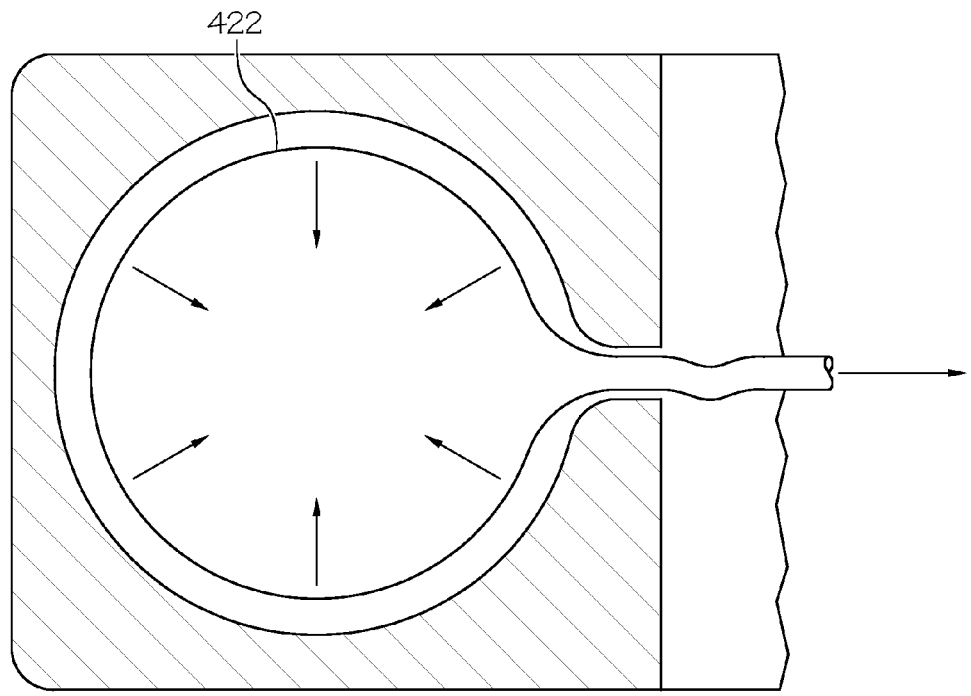
FIG. 7 is a simplified schematic side view of an embodiment of a self-contracting fluid reservoir that resembles a resilient balloon.

FIG. 7 is a simplified schematic side view of another embodiment of a self-contracting fluid reservoir bag that is realized as a self-contracting balloon 422. The balloon 422 is similar to the reservoir bag 412 shown in FIG. 6 in that the balloon 422 naturally tends to "shrink" upon itself, as indicated by the inwardly pointing arrows in FIG. 7. Thus, the balloon 422 expands in volume when filled with the medication fluid, and such expansion inherently places the medication fluid under positive pressure. Accordingly, the medication fluid naturally flows out of the balloon 422 (in the direction indicated by the outgoing arrow) unless the flow is inhibited by the valve assembly of the fluid infusion device. Moreover, the balloon 422 naturally shrinks as the medication fluid exits.

Figure 8:
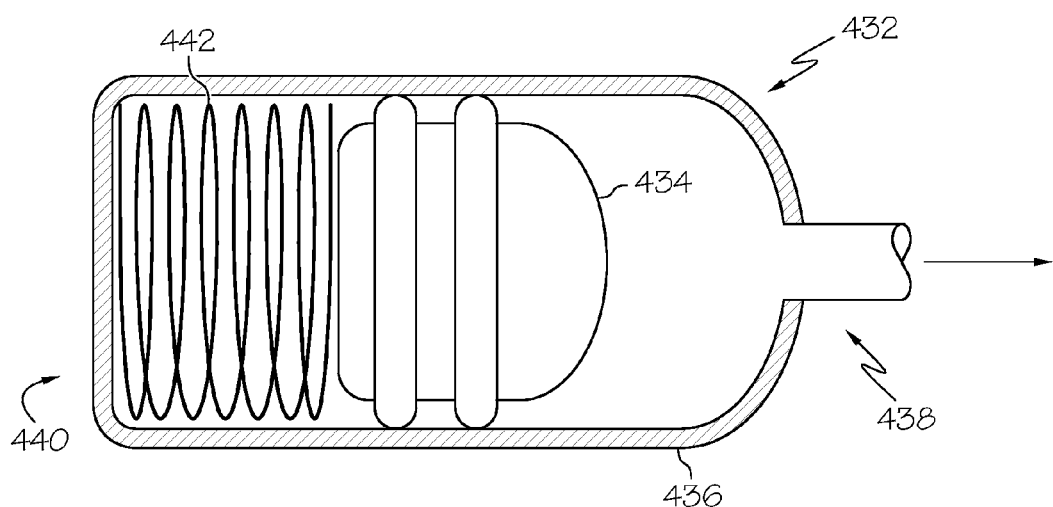
FIG. 8 is a simplified schematic side view of an embodiment of a pressurized fluid reservoir that employs a spring loaded plunger.

FIG. 8 is a simplified schematic side view of an embodiment of a pressurized fluid reservoir 432 that employs a spring loaded plunger 434. The fluid reservoir 432 includes a barrel body 436 (typically having a cylindrical shape) having a fluid delivery end 438 and a base 440 that is opposite the fluid delivery end 438. The plunger 434 is located in the barrel body 436, and the plunger 434 is suitably configured to travel within the barrel body 436. The fluid reservoir 432 also includes a biasing element 442 (e.g., a spring) located in the barrel body 436 between the plunger 434 and the base 440. In accordance with this arrangement, the biasing element 442 biases the plunger 434 toward the fluid delivery end 438. Movement of the plunger 434 toward the fluid delivery end 438 causes the medication fluid to be dispensed from the fluid reservoir 432.

The biasing element 442 cooperates with the plunger 434 to maintain the medication fluid in the fluid reservoir 432 under positive pressure. The tension of the biasing element 442 is low enough to allow filling of the fluid reservoir 432 with the medication fluid. In other words, during a fill operation the biasing element 442 retracts or compresses to allow the plunger 434 to move toward the base 440 to accommodate entry of the medication fluid into the fluid reservoir 432. The biasing element 442 establishes the positive pressure that causes the medication fluid to naturally flow out of the fluid reservoir 432 (in the direction indicated by the arrow) unless the flow is inhibited by the valve assembly of the fluid infusion device.

Figure 9:
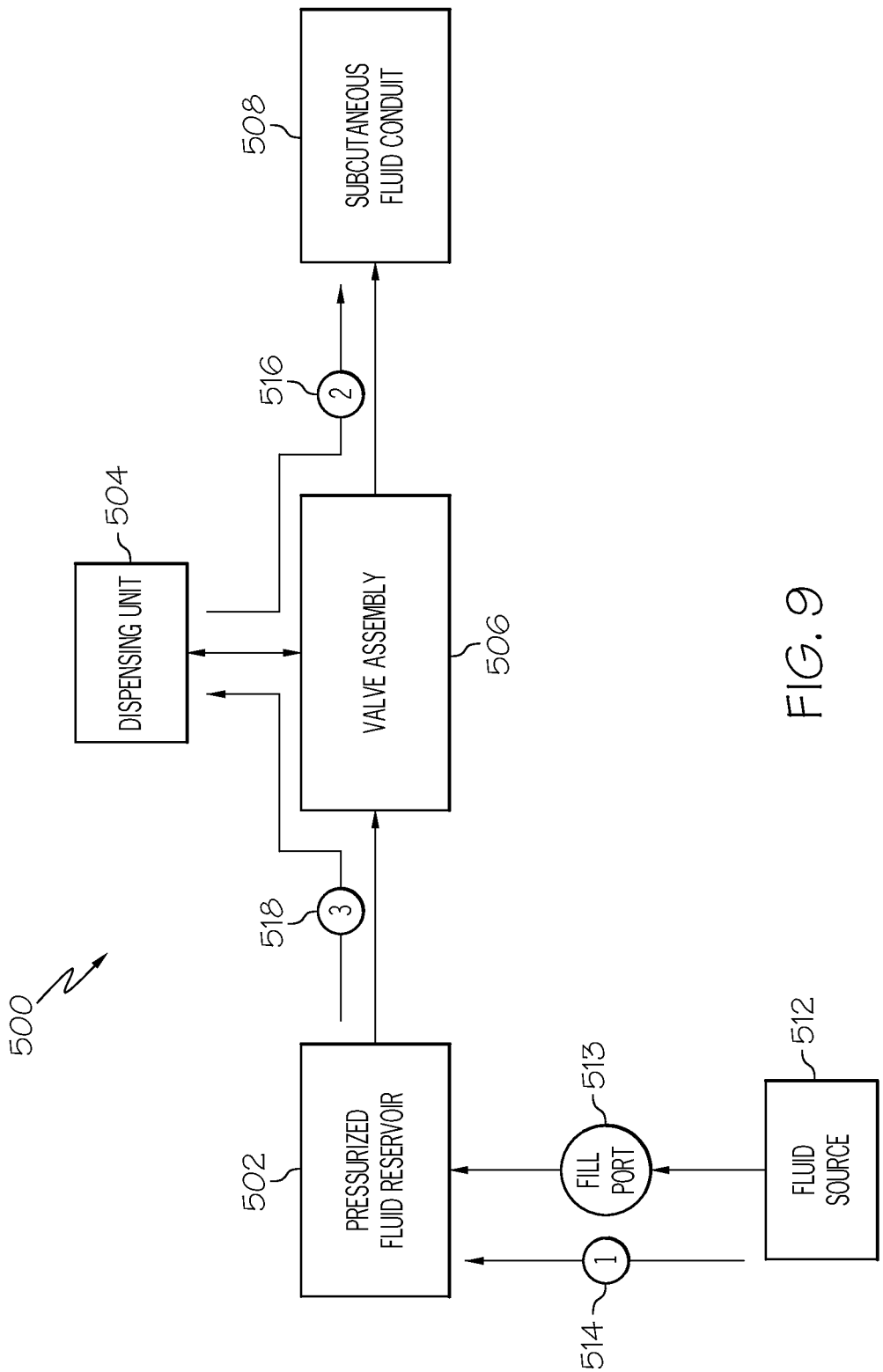
FIG. 9 is a schematic representation of various components of an embodiment of a mechanical fluid infusion device.

An exemplary implementation of a mechanically actuated fluid infusion device employs a pressurized fluid reservoir of the type shown in FIG. 8, along with a valve assembly that regulates fluid flow between the pressurized fluid reservoir, a dispensing unit, and a subcutaneous fluid conduit. In this regard, FIG. 9 is a schematic representation of various components of an embodiment of a mechanical fluid infusion device 500 having at least four primary components: a pressurized fluid reservoir 502; a dispensing unit 504; a valve assembly 506; and a subcutaneous fluid conduit 508. Some of the features, components, and functionality of the fluid infusion device 500 are similar (if not identical) to that described in detail above. For the sake of brevity, common aspects will not be redundantly described here in the context of the fluid infusion device 500.

The pressurized fluid reservoir 502 is physically and fluidly coupled to the valve assembly 506 to accommodate transfer of the medication fluid from the fluid reservoir 502 to the valve assembly 506 as needed. The dispensing unit 504 is also physically and fluidly coupled to the valve assembly 506 to accommodate transfer of the medication fluid from the valve assembly 506 to the dispensing unit 504 (as needed), and to accommodate transfer of the medication fluid from the dispensing unit 504 to the valve assembly 506 (as needed). The fluid conduit 508 is also physically and fluidly coupled to the valve assembly 506 to accommodate transfer of the medication fluid from the valve assembly 506 to the fluid conduit 508. In certain embodiments, the valve assembly 506 is fabricated as a single unitary component having three ports (a first port assigned and coupled to the fluid reservoir 502, a second port assigned and coupled to the dispensing unit 504, and a third port assigned and coupled to the fluid conduit 508). The valve assembly 506 is suitably configured to allow or inhibit fluid flow between the components of the fluid infusion device 500 as needed to support the different functions, operations, and states of the fluid infusion device 500.

The dispensing unit 504 depicted in FIG. 9 represents a subassembly that combines the features and functionality of an adjustable dosing mechanism, a mechanical fluid delivery actuator, and a volume adjuster (as described above with reference to FIG. 4). Accordingly, although not depicted in FIG. 9, the dispensing unit 504 includes an adjustable fluid chamber that defines a user-selectable dosage volume, wherein the amount of medication fluid in the fluid chamber can be delivered in response to mechanical actuation of an actuator.

The following description assumes that the fluid infusion device 500 is designed to accommodate filling of the fluid reservoir 502 by the patient, a caregiver, a doctor, or another person prior to use (i.e., the fluid reservoir 502 is not provided as a prefilled unit). Accordingly, a source 512 of the medication fluid can be fluidly coupled to a fill port 513 of the fluid infusion device 500 to fill the fluid reservoir 502 with the desired amount of the medication fluid. A first flow path 514 represents this filling operation. As explained above with reference to FIG. 8, the fluid reservoir 502 becomes pressurized during the filling operation. During the filling operation, the valve assembly 506 reacts to certain fluid pressure differentials and reconfigures itself to inhibit flow of the medication fluid to the fluid conduit 508. In other words, the valve assembly 506 inhibits flow of the medication fluid from the fluid reservoir 502 such that the fluid source 512 can fill the fluid reservoir 502 in an efficient and safe manner. In certain embodiments, the valve assembly 506 reconfigures itself during the filling operation to inhibit flow of the medication fluid to the dispensing unit 504. In this regard, the valve assembly 506 inhibits flow of the medication fluid from the fluid reservoir 502 to the adjustable fluid chamber of the dispensing unit 504 such that the fluid reservoir 502 can be filled in an efficient and safe manner. In alternative embodiments, the valve assembly 506 reconfigures itself during the filling operation to allow the medication fluid to flow to the dispensing unit 504. In such embodiments, the filling operation may also serve to prime at least a portion of the fluid flow path of the fluid infusion device 500. More specifically, during filling the fluid path between the valve assembly 506 and the fluid conduit 508 is blocked by the valve assembly 506, such that the filling operation primes the fluid pathway except for the segment leading to the fluid conduit 508. This remaining segment can be primed by the user (e.g., by performing one or more fluid delivery actuations) before inserting the fluid conduit 508.

After filling the fluid reservoir 502, filling the fluid chamber of the dispensing unit 504, and priming the flow path of the fluid infusion device 500, a user can manually operate the fluid infusion device as needed to initiate a fluid delivery operation. In response to the application of an external force to the mechanical actuator, the medication fluid is expelled from the dispensing unit 504 to flow through the valve assembly 506 and through the fluid conduit 508. A second flow path 516 represents this fluid delivery operation. During the fluid delivery operation, the valve assembly 506 reacts to certain fluid pressure differentials and reconfigures itself to allow the medication fluid to flow from the adjustable fluid chamber of the dispensing unit 504 into the fluid conduit 508 for delivery to the body of the patient, while concurrently inhibiting flow of the medication fluid from the fluid chamber into the fluid reservoir 502.

Removal of the actuation force from the mechanical actuator of the dispensing unit 504 initiates a refill operation for the fluid infusion device 500. For this particular embodiment, when the external force is removed from the mechanical actuator, the actuator automatically returns to its nominal position. This action creates a pressure differential in the flow path, which in turn refills the fluid chamber of the dispensing unit 504 with medication fluid provided by the pressurized fluid reservoir 502. A third flow path 518 represents this refill operation. During the refill operation, the valve assembly 506 reacts to certain fluid pressure differentials and reconfigures itself to allow the medication fluid to flow from the pressurized fluid reservoir 502 into the fluid chamber of the dispensing unit 504, while concurrently inhibiting flow of the medication fluid from the fluid reservoir 502 to the fluid conduit 508. Moreover, during the refill operation the valve assembly 506 reconfigures itself to inhibit fluid flow from the fluid conduit 508 to the fluid chamber of the dispensing unit 504. After completion of the refill operation, the fluid chamber of the dispensing unit 504 is ready for the next metered delivery of the medication fluid.

Figure 10:
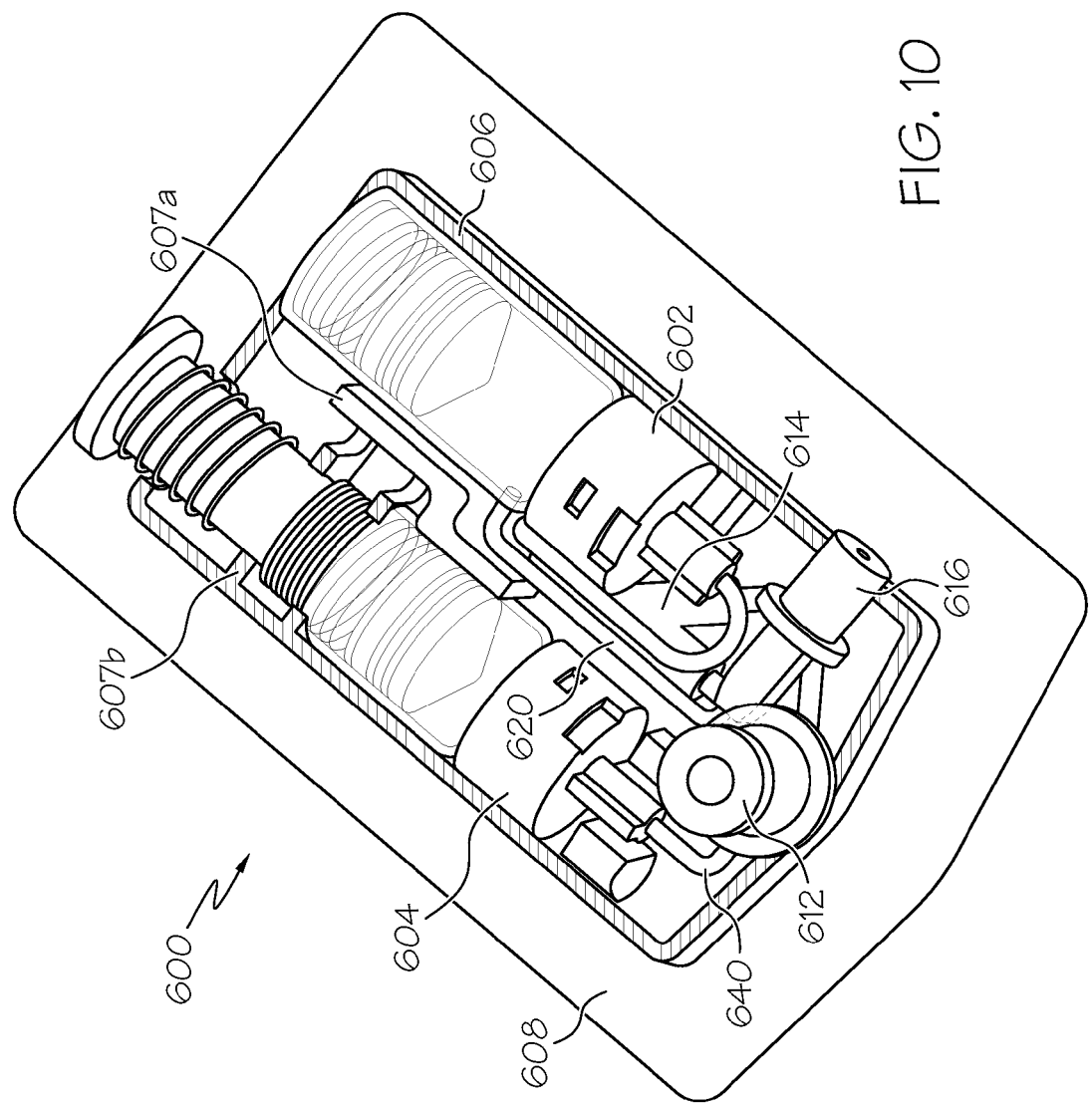
FIG. 10 is a perspective top view of an exemplary embodiment of a mechanically actuated fluid infusion device, with a portion of its housing removed.
Figure 12:
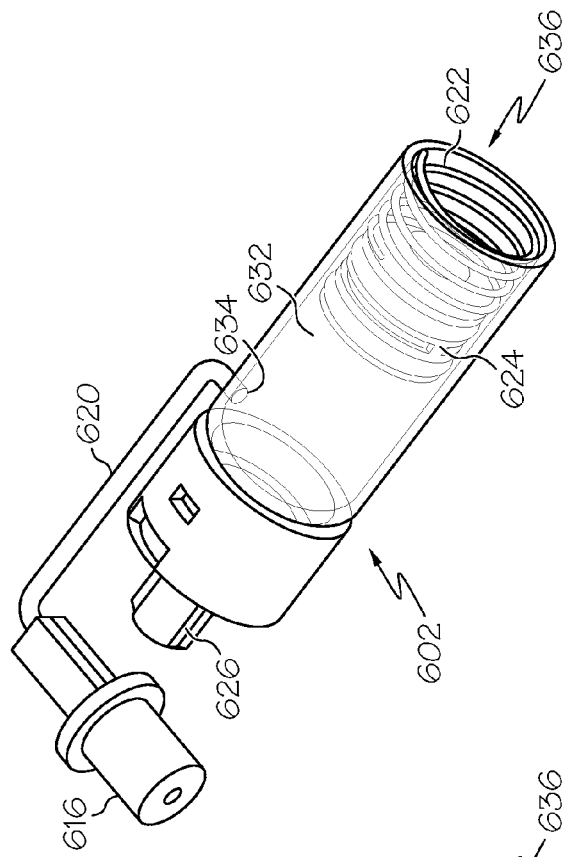
FIG. 12 is a perspective view of the fluid reservoir shown in FIG. 11, after filling with the medication fluid.
Figure 11:
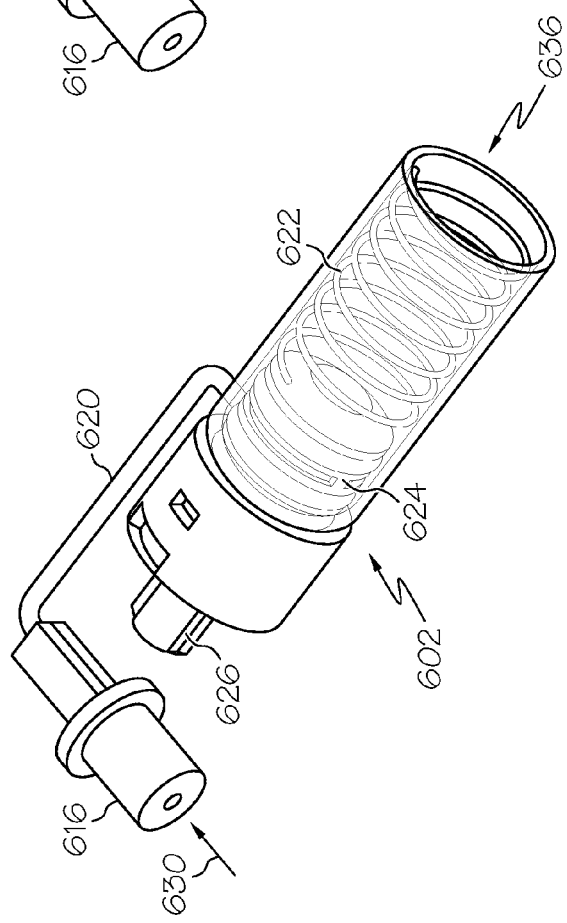
FIG. 11 is a perspective view of a fluid reservoir suitable for use with the fluid infusion device shown in FIG. 10, prior to filling with a medication fluid.
Figure 13:
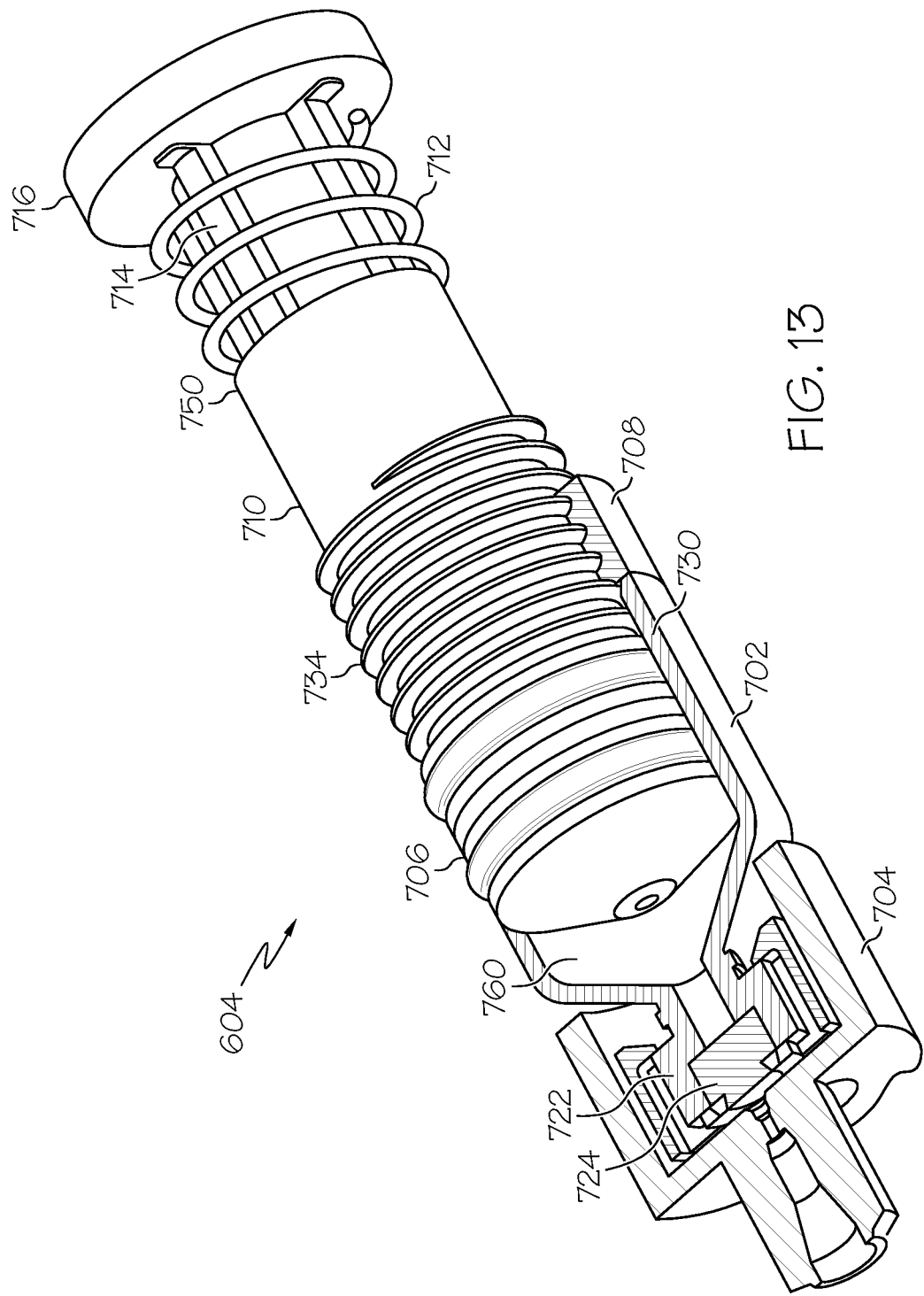
FIG. 13 is a perspective and partially sectioned view of a dispensing unit suitable for use with the fluid infusion device shown in FIG. 10.
Figure 14:
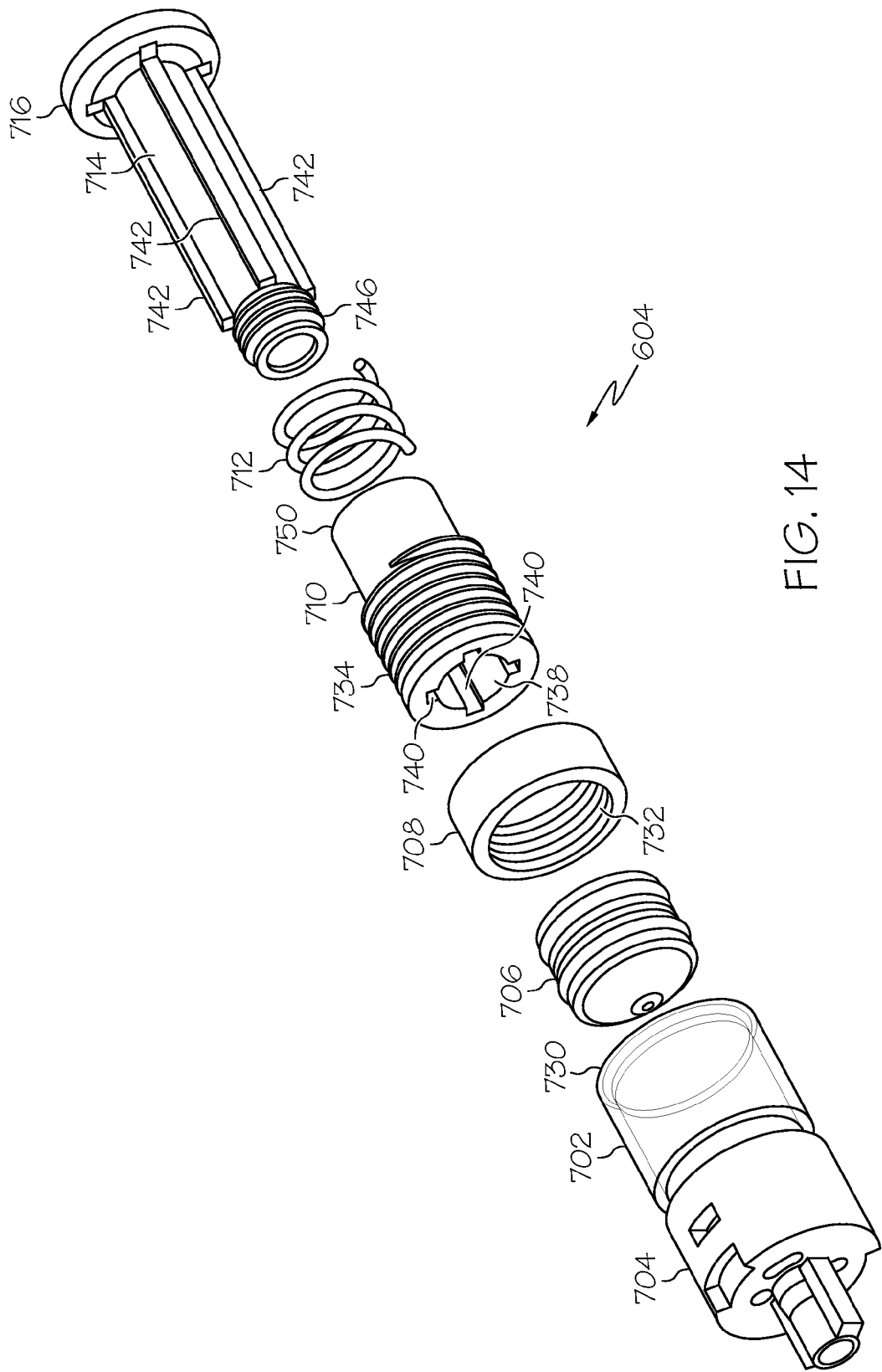
FIG. 14 is an exploded perspective view of the dispensing unit shown in FIG. 13.
Figure 15:
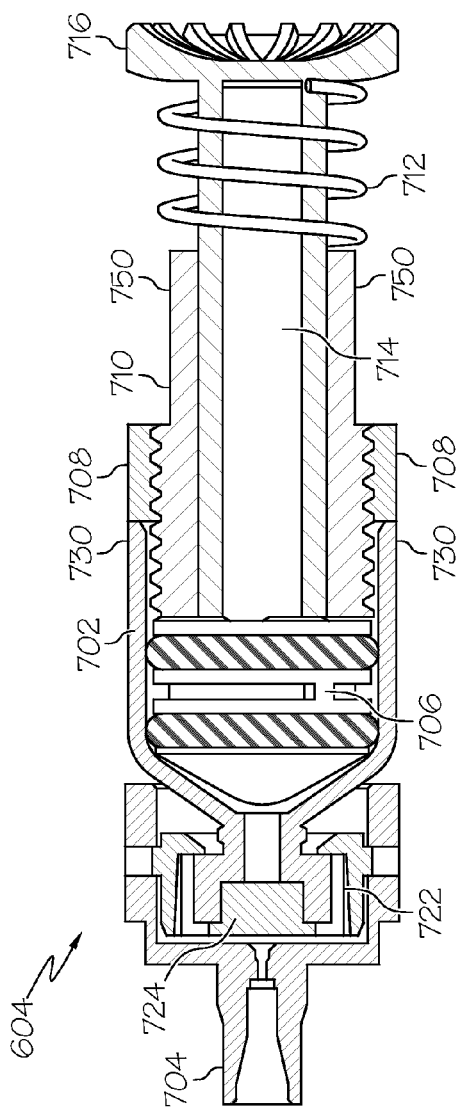
FIGS. 15 and 16 are cross sectional views of the dispensing unit shown in FIG. 13.
Figure 16:
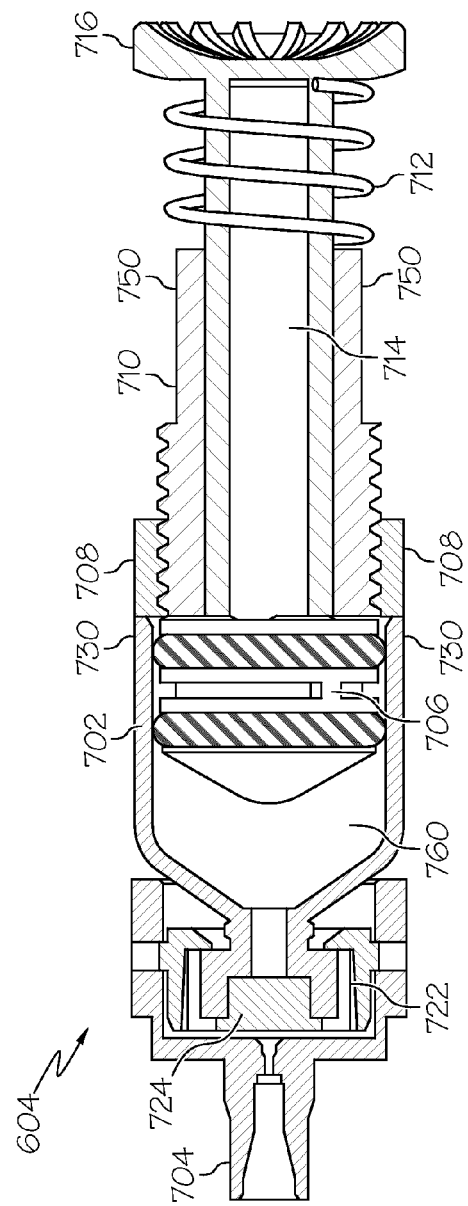

A mechanical fluid infusion device having the features and functions described above can be implemented and realized in any number of ways, using different platforms and form factors as desired. In this regard, FIGS. 10-16 relate to one exemplary implementation of a mechanically actuated fluid infusion device 600. More specifically, FIG. 10 is a perspective top view of the fluid infusion device 600 with a portion of its housing removed, FIG. 11 is a perspective view of a fluid reservoir 602 (in an empty state) of the fluid infusion device 600, FIG. 12 is a perspective view of the fluid reservoir 602 in a filled state, FIG. 13 is a perspective and partially sectioned view of a dispensing unit 604 of the fluid infusion device 600, FIG. 14 is an exploded perspective view of the dispensing unit 604, FIG. 15 is a cross sectional view of the dispensing unit 604 in its nominal state prior to adjustment, and FIG. 16 is a cross sectional view of the dispensing unit 604 in its nominal state after adjustment. It should be appreciated that the fluid infusion device 600 is similar to the fluid infusion device 100 described above with reference to FIG. 1 and FIG. 2. Accordingly, certain features, functions, and aspects that are common to the fluid infusion devices 100, 600 will not be redundantly described here.

The fluid infusion device 600 includes a housing 606 to enclose and protect the internal components. For ease of illustration, the housing 606 in FIG. 10 is shown in cross section. The housing 606 may include or cooperate with certain internal features 607a, 607b that are designed to maintain the internal components of the fluid infusion device 600 in position and/or to provide structural rigidity to the housing 606. The skin-facing side of the fluid infusion device 600 may be coupled to an adhesive patch 608 that accommodates attachment to the skin of the patient.

The fluid infusion device 600 generally includes at least the following functional components: the fluid reservoir 602; the dispensing unit 604; an introducer 612 for a fluid delivery conduit (not shown in FIG. 10); a valve assembly 614; and a fill port 616. As described above with reference to FIG. 9, the valve assembly 614 fluidly and mechanically couples together the fluid reservoir 602, the dispensing unit 604, and the fluid delivery conduit. Although not labeled in FIG. 10, the valve assembly 614 includes or cooperates with suitably shaped and configured conduits that route the respective fluid flow paths between the components. In certain embodiments, the valve assembly 614 may be realized as a three-way valve having an internal ball that moves in response to fluid pressure differentials to regulate the incoming and outgoing fluid flow paths as needed. The fill port 616 is fluidly and structurally coupled to the fluid reservoir 602 via a filling conduit 620.

Referring to FIG. 11 and FIG. 12, the fluid reservoir 602, the fill port 616, and the filling conduit 620 are depicted in an isolated manner. The illustrated embodiment of the fluid reservoir 602 is a self-pressurizing unit that is similar to the fluid reservoir 432 described above with reference to FIG. 8. FIG. 11 shows the fluid reservoir 602 in an empty state, and FIG. 12 shows the fluid reservoir 602 in a filled state. In the empty state, a spring 622 (or any suitable biasing element) forces a plunger 624 upward and toward an outlet port 626 of the fluid reservoir 602. In accordance with one exemplary filling operation, a needle of a filling source can be inserted into the fill port 616 (as indicated by the arrow 630 in FIG. 11) such that the medication fluid can be forced under pressure into a chamber 632 of the fluid reservoir 602. The fill port 616 may include a septum or other type of sealing element that accommodates the fill needle and forms a fluid seal after the fill needle is removed. As shown in FIG. 12, the chamber 632 may be defined as the space between the top of the plunger 624 and the outlet port 626. The filling conduit 620 may terminate at an opening 634 that is located above the plunger 624 when the fluid reservoir 602 is in the empty state. Consequently, the medication fluid fills the chamber 632, while urging the plunger 624 downward and toward a base 636 of the fluid reservoir 602. During the filling operation, the spring 622 becomes compressed, which in turn pressurizes the fluid reservoir 602 to maintain the medication fluid under positive pressure. The spring 622 preferably keeps the medication fluid under constant pressure until the chamber 632 is empty (or near empty) for practical purposes. Upon completion of the filling operation, the needle is removed from the fill port 616 such that the fluid infusion device 600 can be prepared for use.

The dispensing unit 604 may be coupled to the valve assembly 614 via a dispensing conduit 640 (see FIG. 10). For this particular embodiment, the dispensing unit 604 represents a subassembly that incorporates the structure and functionality of an adjustable fluid chamber, a dosing mechanism, a mechanical delivery actuator, and a volume adjuster for the adjustable fluid chamber. FIGS. 13-16 depict an exemplary embodiment of the dispensing unit 604 in greater detail.

The illustrated embodiment of the dispensing unit 604 includes, without limitation: a reservoir barrel 702; a fitting 704 for the reservoir barrel 702; a plunger stopper 706; a dosage guide 708; a dosage knob 710; a spring 712 (or other suitable biasing element); and an actuator stem 714, which may include, cooperate with, or be coupled to an actuation knob 716. These elements of the dispensing unit 604 are coupled together or otherwise cooperate with one another to form a subassembly having the desired features and functionality described here.

The reservoir barrel 702 forms a part of the adjustable fluid volume that holds the desired metered amount of medication fluid for delivery to the patient. In certain embodiments, the reservoir barrel 702 may have a cylindrical cross section, and it may resemble the end portion of a syringe. The reservoir barrel 702 may terminate at a port 722, which in turn may be coupled to the fitting 704. The fitting 704 cooperates with the port 722 to establish a physical and fluid connection between the dispensing unit 604 and the valve assembly 614 (see FIG. 10). Although not shown, the fitting 704 may employ a hollow needle that pierces a septum 724 located in the port 722, wherein the hollow needle establishes a fluid flow path to and from the interior of the reservoir barrel 702.

The dosage guide 708 may be affixed to a base 730 of the reservoir barrel 702, as shown in FIGS. 13, 15, and 16. For example, the rim of the dosage guide 708 could be glued, bonded, welded, or otherwise secured to the base 730 of the reservoir barrel 702 to form an integrated component. As shown in FIG. 14, the dosage guide 708 resembles a ring with internal threads 732. The internal threads 732 mate with and engage corresponding external threads 734 formed on the dosage knob 710. The purpose and function of this threaded engagement are described in more detail below with reference to FIGS. 15 and 16.

The dosage knob 710 includes a longitudinal opening 738 formed therein to receive and accommodate the actuator stem 714. The longitudinal opening 738 is formed completely through the dosage knob 710 to allow passage of the actuator stem 714 (see FIGS. 15 and 16). Notably, the dosage knob 710 and the actuator stem 714 are cooperatively configured to accommodate translation of the actuator stem 714 relative to the dosage knob 710, while inhibiting rotation between the dosage knob 710 and the actuator stem 714. Thus, the actuator stem 714 is free to slide within the dosage knob 710 between a nominal position and an actuated position. However, rotation of the actuator stem 714 results in a corresponding rotation of the dosage knob 710, and vice versa. The illustrated embodiment achieves this functionality with a key/keyway arrangement. In this regard, the longitudinal opening 738 may define one or more keyways 740 that receive and cooperate with one or more counterpart keys 742 that protrude from the actuator stem 714. Although not always required, the embodiment described here employs four keyways 740 and four cooperating keys to inhibit rotation of the actuator stem 714 relative to the dosage knob 710. The keyway/key arrangement is suitably designed to allow translational movement of the actuator stem 714 within the longitudinal opening 738 of the dosage knob 710.

The actuator stem 714 terminates at a plunger end 746 that is suitably configured to mate with and couple to the plunger stopper 706. In certain embodiments, the plunger end 746 is threaded to mate with corresponding threads of the plunger stopper 706. The illustrated embodiment employs an externally threaded plunger end 746 that screws into an internally threaded cavity (not shown) of the plunger stopper 706. FIGS. 13, 15, and 16 depict the dispensing unit 604 after the plunger stopper 706 has been screwed onto the actuator stem 714.

The spring 712 is installed over the actuator stem 714 such that it remains positioned between the actuation knob 716 and an end 750 of the dosage knob 710. When the dispensing unit 604 is assembled, the spring 712 serves as a biasing element for the mechanical actuator, such that the spring 712 biases the actuator stem 714 and the plunger stopper 706 into a nominal pre-delivery position (see FIG. 13 and FIG. 16). In practice, the spring 712 is compressed during a fluid delivery stroke such that it automatically springs back and moves the actuator stem 714 back into the nominal pre-delivery position following each operation of the mechanical actuator.

The dispensing unit 604 may be assembled in the following manner. The spring 712 is placed onto the actuator stem 714, followed by the dosage knob 710. The dosage guide 708 is threaded onto the dosage knob 710 (either before or after the dosage knob 710 is placed onto the actuator stem 714, as desired). Next, the plunger stopper 706 is threaded onto the actuator stem 714 (and, if necessary, glued or otherwise affixed to the plunger stopper 706). It may be necessary to move the actuator stem 714 and compress the spring 712 somewhat to expose the plunger end 746 of the actuator stem 714 before attaching the plunger stopper 706 to the plunger end 746. Thereafter, the plunger stopper 706 can be introduced into the reservoir barrel 702, and the rim of the dosage guide 708 can be affixed to the base 730 of the reservoir barrel 702, resulting in the arrangement shown in FIGS. 13, 15, and 16.

As explained above, the dispensing unit 604 can be manipulated to vary the volume of an adjustable fluid chamber 760 (see FIG. 13 and FIG. 16). FIG. 15 depicts the state of the dispensing unit 604 with a minimum volume defined for the adjustable fluid chamber 760, and FIG. 16 depicts the state of the dispensing unit 604 with a maximum volume defined for the adjustable fluid chamber 760. For this particular embodiment, the user-selectable dosage volume is adjusted in response to rotation of the actuator stem 714 and/or rotation of the actuation knob 716. Such rotation corresponds to rotation of the actuator stem 714 about its major longitudinal axis. Referring to FIGS. 13, 15, and 16, rotation of the actuation knob 716 results in rotation of the actuator stem 714, which in turn results in rotation of the dosage knob 710. Rotation of the dosage knob 710 causes the dosage knob 710 to translate relative to the dosage guide 708 (the translation is depicted in FIG. 15 and FIG. 16). Translational movement of the dosage knob 710 alters the nominal pre-delivery and post-delivery position of the plunger stopper 706, which in turn changes the nominal pre-delivery and post-delivery dosage volume of the fluid chamber 760. Notably, the force imparted by the spring 712 causes the actuation knob 716 to be biased away from the end 750 of the dosage knob 710, and this biasing action sets the actuator stem 714 and the plunger stopper 706 into the desired position that defines the fluid chamber 760.

The dispensing unit 604 is actuated in response to the application of force in a direction that is aligned with the major longitudinal axis of the actuator stem 714. In practice, the dispensing unit 604 is actuated when the user presses the actuation knob 716 down. Fully depressing the actuator stem 714 results in the delivery of the metered and calibrated amount of medication fluid contained in the fluid chamber 760. As explained previously, the fluid reservoir 602 (see FIG. 10) automatically refills the adjustable fluid chamber 760 with the medication fluid in response to the spring 712 returning the actuator stem 714 into the nominal pre-delivery position.

In certain embodiments, the dispensing unit 604 is designed to provide tactile and/or audible feedback to the user while the fluid chamber 760 is being adjusted. For example, the dispensing unit 604 may employ detents or tabs to provide "clicks" or other feedback that indicates a predefined volume graduation, e.g., 0.2 Units, 0.5 Units, or 1.0 Unit per click. Thus, adjustment of the dosage volume can be easily achieved by counting the number of clicks as the actuation knob 716 is being rotated (assuming that the adjustment operation begins at a known reference volume). Moreover, numerical or other indicia could be printed on the dosage knob 710 and/or elsewhere to indicate the dosage volume during the adjustment operation. As described above with reference to FIG. 1, the housing 102 may include an opening 108 that allows the user to see the volume indicator(s) during the adjustment operation.

The dispensing unit 604 may also include a feature that locks the adjustment component(s) to inhibit rotation of the actuator stem 714 after the desired dosage volume has been selected. Accordingly, once set, the metered dosage volume remains fixed until the user or caregiver adjusts the volume again. Thereafter, the medication fluid can be delivered in metered increments by activating the actuation knob 716, until the medication fluid is depleted. At that time, the entire fluid infusion device can be discarded. In certain alternative embodiments, the fluid reservoir can be refilled via the fill port to extend the useful life of the fluid infusion device.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device for delivery of a medication fluid to the body of a user, the fluid infusion device comprising:
   a housing;
   a fluid reservoir for the medication fluid, wherein the fluid reservoir is located in the housing, and wherein the medication fluid in the fluid reservoir is maintained under positive pressure;
   a valve assembly located in the housing and coupled to the fluid reservoir;
   a dosing mechanism located in the housing and coupled to the fluid reservoir via the valve assembly, the dosing mechanism comprising an adjustable fluid chamber that defines a user-selectable dosage volume, and the dosing mechanism comprising a mechanical actuator; and
   a fluid conduit coupled to the dosing mechanism via the valve assembly, wherein at least a portion of the fluid conduit is external to the housing when the fluid infusion device is deployed for operation; wherein:
   application of an actuation force to the mechanical actuator initiates a fluid delivery operation;
   removal of the actuation force from the mechanical actuator initiates a refill operation;
   during the fluid delivery operation, the valve assembly allows the medication fluid to flow from the adjustable fluid chamber into the fluid conduit for delivery to the body of the patient, while inhibiting flow of the medication fluid from the adjustable fluid chamber into the fluid reservoir; and
   during the refill operation, the valve assembly allows the medication fluid to flow from the fluid reservoir into the adjustable fluid chamber, while inhibiting flow of the medication fluid from the fluid reservoir into the fluid conduit.

2. The fluid infusion device of claim 1, wherein:
   the valve assembly inhibits flow of the medication fluid from the fluid conduit to the fluid reservoir; and
   the valve assembly inhibits flow of the medication fluid from the fluid conduit to the adjustable fluid chamber.

3. The fluid infusion device of claim 1, wherein the fluid reservoir comprises a self-contracting reservoir bag.

4. The fluid infusion device of claim 1, wherein the fluid reservoir comprises:
   a resilient bladder; and
   a structure operatively coupled to the resilient bladder to impart a compressive force to the resilient bladder.

5. The fluid infusion device of claim 1, wherein the fluid reservoir comprises:
   a barrel body having a fluid delivery end and a base opposite the fluid delivery end;
   a plunger located in the barrel body; and
   a biasing element located in the barrel body between the plunger and the base of the barrel body, wherein the biasing element biases the plunger toward the fluid delivery end.

6. The fluid infusion device of claim 1, wherein the adjustable fluid chamber is adjustable in discrete steps that define a plurality of predetermined and calibrated dosage volumes.

7. The fluid infusion device of claim 1, further comprising an adhesive patch having a first side affixed to the housing and a second side for attachment to the body of the patient.

8. The fluid infusion device of claim 1, further comprising a fill port accessible from outside the housing, wherein:
   the fill port is fluidly coupled to the fluid reservoir to facilitate filling of the fluid reservoir with the medication fluid during a filling operation; and
   during the filling operation, the valve assembly inhibits flow of the medication fluid from the fluid reservoir to the fluid conduit.

9. A fluid infusion device for delivery of a medication fluid to the body of a user, the fluid infusion device comprising:
   a housing;
   a fluid reservoir to maintain the medication fluid under positive pressure, wherein the fluid reservoir is located in the housing;
   a valve assembly located in the housing and coupled to the fluid reservoir;
   a dosing mechanism located in the housing and coupled to the fluid reservoir via the valve assembly, the dosing mechanism comprising a mechanical actuator to adjust a fluid chamber of the dosing mechanism such that the fluid chamber defines a user-selectable dosage volume; and
   a fluid delivery conduit coupled to the dosing mechanism via the valve assembly;
   wherein:
   in response to application of force to the mechanical actuator, the medication fluid in the fluid chamber is expelled through the fluid delivery conduit, while the valve assembly inhibits flow of the medication fluid from the fluid chamber to the fluid reservoir; and
   in response to removal of the force, the mechanical actuator automatically retracts to refill the fluid chamber with the medication fluid from the fluid reservoir, while the valve assembly inhibits flow of the medication fluid from the fluid reservoir to the fluid delivery conduit and inhibits fluid flow from the fluid delivery conduit to the fluid chamber.

10. The fluid infusion device of claim 9, wherein the user-selectable dosage volume is adjustable in discrete steps that define a plurality of predetermined and calibrated dosage volumes.

11. The fluid infusion device of claim 9, wherein:
the user-selectable dosage volume is adjusted in response to rotation of the mechanical actuator about a major longitudinal axis; and
the mechanical actuator is actuated in response to application of the force in a direction aligned with the major longitudinal axis.

12. The fluid infusion device of claim 9, wherein the fluid reservoir comprises a self-contracting reservoir bag.

13. The fluid infusion device of claim 9, wherein the fluid reservoir comprises:
a resilient bladder; and
a structure operatively coupled to the resilient bladder to impart a compressive force to the resilient bladder.

14. The fluid infusion device of claim 9, wherein the fluid reservoir comprises:
a barrel body having a fluid delivery end and a base opposite the fluid delivery end;
a plunger located in the barrel body; and
a biasing element located in the barrel body between the plunger and the base of the barrel body, wherein the biasing element biases the plunger toward the fluid delivery end.

15. The fluid infusion device of claim 9, further comprising an adhesive patch having a first side affixed to the housing and a second side for attachment to the body of the patient.

* * * * *